(12) United States Patent
Strauss et al.

(10) Patent No.: US 6,726,895 B2
(45) Date of Patent: Apr. 27, 2004

(54) METHOD OF IMAGING CELL DEATH IN VIVO

(75) Inventors: H. William Strauss, Redwood City, CA (US); Francis G. Blankenberg, Menlo Park, CA (US); Allan M. Green, Cambridge, MA (US); Neil Steinmetz, Atlantis, FL (US)

(73) Assignees: Board of Trustees of the Leland Stanford Junior University, Palo Alto, CA (US); Theseus Imaging Corporation, Boston, MA (US)

( * ) Notice: Subject to any disclaimer, the term of this patent is extended or adjusted under 35 U.S.C. 154(b) by 0 days.

(21) Appl. No.: 10/114,926

(22) Filed: Apr. 3, 2002

(65) Prior Publication Data

US 2003/0003047 A1 Jan. 2, 2003

Related U.S. Application Data

(60) Provisional application No. 60/281,352, filed on Apr. 3, 2001.

(51) Int. Cl.$^7$ .......................... A61K 51/00; A61M 36/14
(52) U.S. Cl. .................... 424/1.69; 424/1.11; 424/1.65; 424/9.1
(58) Field of Search ............................... 424/1.11, 1.65, 424/1.69, 9.1; 530/350

(56) References Cited

U.S. PATENT DOCUMENTS

| | | | |
|---|---|---|---|
| 4,671,256 A | 6/1987 | Lemelson | 128/1.1 |
| 5,519,221 A | 5/1996 | Weinberg | 250/363.02 |
| 5,552,525 A | 9/1996 | Dean | 530/326 |
| 5,627,036 A | 5/1997 | Reutelingsperger | 435/7.21 |
| 5,632,986 A | 5/1997 | Tait et al. | 424/94.64 |
| 5,776,427 A | 7/1998 | Thorpe et al. | 424/1.49 |
| 5,855,866 A | 1/1999 | Thorpe et al. | 424/1.49 |
| 5,863,538 A | 1/1999 | Thorpe et al. | 424/136.1 |
| 5,955,437 A | 9/1999 | Reutelingsperger | 514/21 |
| 5,965,132 A | 10/1999 | Thorpe et al. | 424/149 |
| 5,968,477 A | 10/1999 | Kasina et al. | 424/1.69 |
| 6,004,554 A | 12/1999 | Thorpe et al. | 424/178.1 |
| 6,051,230 A | 4/2000 | Thorpe et al. | 424/178.1 |
| 6,171,577 B1 * | 1/2001 | Kasina et al. | 424/1.69 |
| 6,197,278 B1 * | 3/2001 | Blankenberg et al. | 424/1.69 |
| 6,261,535 B1 | 7/2001 | Thorpe et al. | 424/1.49 |
| 6,312,694 B1 | 11/2001 | Thorpe et al. | 424/178.1 |
| 6,323,313 B1 | 11/2001 | Tait et al. | 530/324 |
| 6,406,693 B1 | 6/2002 | Thorpe et al. | 424/130.1 |
| 2002/0192162 A1 * | 12/2002 | Green | 424/9.4 |

FOREIGN PATENT DOCUMENTS

| | | |
|---|---|---|
| WO | WO 92/19279 | 11/1992 |
| WO | WO 94/10149 | 5/1994 |
| WO | WO 95/27903 | 10/1995 |
| WO | WO 95/34315 | 12/1995 |
| WO | WO 96/17618 | 6/1996 |
| WO | WO 98/04294 | 2/1998 |
| WO | WO 00/02587 A1 | 1/2000 |
| WO | WO 00/02584 A2 A3 | 1/2000 |

OTHER PUBLICATIONS

Blankenberg et al (2001), J. Nuclear Medicine, vol. 42, No. 2, pp. 309–316.*

Ohtsuki et al (Oct. 1999), European Journal of Nuclear Medicine, vol. 26, No. 10, pp. 1251–1258.*

Babich, J.W., et al., "Technetium–99m–Labeled Hydrazino Nicotinamide Derivatized Chemotactic Peptide Analogs for Imaging Focal Sites of Bacterial Infection," *The Journal of Nuclear Medicine* 34(11):1964–1974 (1993).

Barrow, S.A., et al., "Localization of Indium–111–Immunoglobulin G, Technetium–99m– Immunoglobulin G and Indium–111–Labeled White Blood Cells at Sites of Acute Bacterial Infection in Rabbits," *The Journal of Nuclear Medicine* 34(11):1975–1979 (1993).

Bennett, M.R., et al., "Binding and Phagocytosis of Apoptotic Vascular Smooth Muscle Cells Is Mediated in Part by Exposure of Phosphatidylserine," *Circ. Res.* 77(6): 1136–1142 (1995).

Blankenberg, F.G., et al., "Detection of Apoptotic Cell Death by Proton Nuclear Magnetic Resonance Spectroscopy," *Blood* 87(5):1951–1956 (1996).

Kasina, S., et al., "Preformed Chelate TC–99m Radiolabeling of r–Annexin V for Arterial Thrombus Imaging," *J. of Nuclear Medicine, Proceedings of the 43$^{rd}$ Annual Meeting* 37(5 Supp.):29P Abstract No. 106 (1996).

Koopman, G., et al., "Annexin V for Flow Cytometric Detection of Phosphatidylserine Expression on B Cells Undergoing Apoptosis," *Blood* 84(5): 1415–1420 (1994).

Reutelingsperger, C.P.M. et al., "Annexin V, the regulator of phosphatidylserine–catalyzed inflammation and coagulation during apoptosis," *Cell. Mol. Life Sci.* 53:527–532 (1997).

Schwartz, D.A., et al. "Preparation of Hydrazino–Modified Proteins and Their Use for the Synthesis of $^{99m}$Tc–Protein Conjugates," *Bioconjugate Chem.* 2: 333–336 (1991).

Stratton, J.R., et al., "Selective Uptake of Radiolabeled Annexin V on Acute Porcine Left Atrial Thrombi," *Circulation* 92: 3113–3121 (1995).

Tait, J.F., et al., "Site–Specific Mutagenesis of Annexin V: Role of Residues from Arg–200 to Lys–207 in Phospholipid Binding," *Archives of Biochem. and Biophys.* 288(1):141–144 (1991).

Tait, J.F., et al., "Measurement of membrane phospholipid asymmetry in normal and sickle–cell erthrocytes by means of annexin V binding," *J.Lab. Clin. Med.* 123(5):741–748 (1994).

(List continued on next page.)

Primary Examiner—Dameron L. Jones
(74) Attorney, Agent, or Firm—Lahive & Cockfield, LLP; Giulio A. DeConti, Jr.; Maria Laccotripe Zacharakis

(57) ABSTRACT

A method of imaging apoptosis in vivo, using radiolabeled annexin, is described. Methods for tumor radiotherapy are also provided.

17 Claims, 3 Drawing Sheets

OTHER PUBLICATIONS

Tait, J.F., et al., "Phospholipid Binding Properties of Human Placental Anticoagulant Protein–I, a Member of the Lipocortin Family," *The Journal of Biological Chemistry* 264(14):7944–7949 (1989).

Tait, J.F., et al., "Placental Anticoagulant Proteins: Isolation and Comparative Characterization of Four Members of the Lipocortin Family," *Biochemistry* 27:6268–6276 (1988).

Tait, J. F., "Clinical Applications of Annexins," *Annexins: Molecular Structure to Cellular Function*, ed. Barbara A. Seaton, R.G. Landes Co., pp. 213–220 (1996).

van Heerde, W.L., et al., "The Complexity of the Phospholipid Binding Protein Annexin V," *Thrombosis and Haemostasis* 73(2):172–179 (1995).

Wood, B.L., et al., "Increased Erythrocyte Phosphatidylserine Exposure in Sickle Cell Disease: Flow–Cytometric Measurement and Clinical Associations," *Blood* 88(5): 1873–1880 (1996).

Zwaal, R.F.A., et al., "Pathophysiologic Implications of Membrane Phospholipid Asymmetry in Blood Cells," *Blood* 89(4): 1121–1132 (1997).

* cited by examiner

METHOD OF IMAGING CELL DEATH IN VIVO

RELATED APPLICATIONS

This application claims priority to U.S. Provisional Patent Application Serial No. 60/281,352 filed Apr. 3, 2001, the entire contents of which are incorporated herein by reference.

This work was supported in part by NIH Grant HL-47151. Accordingly, the United States Government has certain rights in this invention.

FIELD OF THE INVENTION

The present invention relates to a method of imaging cell death in vivo. In particular, it relates to the use of radiolabeled annexin to image regions of cell death in a mammal using gamma ray imaging.

REFERENCES

Amann, E. and Brosius, J., *Gene* 40:183 (1985).
Asselin, B. L., et al., *Cancer Res.* 49:4363 (1989).
Ausubel, F. M., et al., *Current Protocols in Molecular Biology* (John Wiley and Sons, Inc., Media, Pa.).
Babich, J. W., et al., *Journal of Nuclear Medicine* 34:1964 (1993).
Ballon, D., et al., *Magn. Reson. Med.* 19:85 (1991).
Barrow, S. A., et al., *J. Nucl. Med.* 34:1975 (1993).
Beames, et al., *Biotechniques* 11:378 (1991).
Bindl, J. M. & Warnke, R. A., *Am. J. Clin. Pathol.* 85:490–493 (1986).
Blankenberg, F. G., et al., *Blood* 87:1951 (1996).
Borenstain-Ben Yashar, V., et al., *Am. J. Hematol.* 44:63 (1993).
Connor, J., et al., *J. Biol. Chem.* 267:19412 (1992).
D'Amico, A. V., and McKenna, W. G., *Radiotherapy and Oncology* 33:3 (1994).
Darzynkiewicz, Z., J. of *Cell Biochem.* 58:151 (1995).
Darzynkiewicz, Z., et al., *Methods in Cell Biology* 41:15 (1994).
Dive, C., et al., *Biochim et Biophys Acta* 1133:275 (1992).
Du, C., et al., *J. Cereb. Blood Flow and Metab.* 16: 195–201 (1996).
Fadok, V. A., et al., *J. of Immunol.* 148:2207 (1992).
Fadok, V. A., et al., *J. of Immunol.* 149:4029 (1992).
Fadok, V. A., et al., *J. of Immunol.* 151:4274 (1993).
Fischman, et al., *J. Nucl. Med.* 32:482–491 (1991).
Funakoshi, T., et al., *Biochemistry* 26:5572 (1987).
Funk, G. M., et al., *J. Lipid Res.* 27:792 (1986).
Gavrieli, Y., et al., *J. Cell Biol.* 119:493 501 (1992).
Geng, Y. -J., et al., *Arteriosclerosis, Thrombosis, and VascularBiol.* 15:1995 (1995).
Harlow, E., et al., ANTIBODIES: A LABORATORY MANUAL, Cold Spring Harbor Laboratory Press (1988).
Hnatowich, D. J., et al., *J. Immunol. Meth.* 65:147 (1983).
Jensen, K. E., et al., *Magr'. Reson. Imaging* 8:779 (1990).
Koopman, G., et al., *Blood* 84(5):1415–1520 (1994).
Lacronique, V., et al., *Nature Med.* 2(1):80 (1996).
LaMuraglia, et al., *J. Vasc. Surg.* 10:20–28 (1989).
Lane, A., et al., *Am. J. Hematol.* 47:295 (1994).
Larson, S. K., et al., *Biocor~jugate Chem.* 6:635–638 (1995).
Lind, et al., *J. Nucl. Med.* 31:417–473 (1990).
Maloney, D. G., et al., *Hybridoma* 4:191–209 (1985).
Martin, S. J., et al., *J. Exp. Med.* 182:1545 (1995).
May, G. L., et al., *J. Biochem.* 261:3048 (1986).
Mettler, F. A. and M. J. Guiberteau, ESSENTIALS OF NUCLEAR MEDICINE IMAGING, Second Edition, W. B. Saunders Company, Philadelphia, Pa. (1985).
Mirkovic, N., et al., *Radiotherapy and Oncology* 33:11 (1994).
Mitchell, K. T., et al., *Anal. Biochem.* 158:447 (1986).
Mombers, C., et al., *Biochem et Biophys Acta* 551:271 (1979).
Mountford, C. E., and Tattersall, M. H. N., *Cancer Surv.* 6:285 (1987).
Mulkern, R. V., et al., *J. Magn. Reson. Imaging* 4:585 (1994).
Mullis, K. B., et al., U.S. Pat. No. 4,683,195, issued Jul. 28, 1987.
Mullis, K. B., U.S. Pat. No. 4,683,202, issued Jul. 28, 1987.
Narula, J., et al., *New Engl. J. Med.* 335:1182 (1996).
Naumovski, L., and Cleary, M. L., *Blood* 83:2261 (1994).
Niemeyer, C. M., et al., (Protocol 81-01 Update) *Blood* 78:2514 (1991).
Ogasawara, J., et al., *Nature* 364:806 (1993).
Pak, C. C. and I. J. Fidler, *Semin. Cancer Biol.* 2:189 (1991).
Perillo, N. L., et al., *Nature* 378:736 (1995).
Reilly, P. R., et al., in BACULOVIRUS EXPRESSION VECTORS: A LABORATORY MANUAL (1992).
Rodriguez, I., et al., *J. Exp. Med.* 184:2067–2072 (1996).
Sambrook, J., et al., MOLECULAR CLONING: A LABORATORY MANUAL, Second Edition, Cold Spring Harbor Laboratory, Cold Spring Harbor, N.Y. (1989).
Schick, F., et al., *Magn. Reson. Med.* 26:207 (1992).
Schwartz, D. A., et al., *Bioconjugate Chem.* 2:333 (1991).
Seigneuret, M., and P. F. Devaux, *Proc. National Acad. Sci. USA* 81:3751 (1984).
Seiter, K., et al., *Leukemia* 2:1961 (1995).
Smith, D. B., et al., *Gene* 67:31 (1988).
Stark, R. E., et al., *J. of Physical Chemistry* 89:272 (1985).
Stark, R. E., et al., *Biochemica et Biophysica Acta* 860:399 (1986).
Stephens, L. C., et al., *Radiation Res.* 135:75 (1993).
Stratton, J. R., et al., *Circulation* 92:3113–3121 (1995).
Tait, J. F., "Clinical Applications of Annexins," in ANNEXINS: MOLECULAR STRUCTURE TO CELLULAR FUNCTION(Seaton, B. A., Ed.) R. G. Landes Company (1996).
Tait, J. F. and Gibson, D., *J. Lab. Clin. Med.* 123:741 (1994).
Tait, J. F. and Smith, C., *Arch. Biochem. Biophys.* 288:141 (1991).
Tait, J. F., et al., *J. Biol. Chem.* 264:7944 (1989).
Tait, J. F., et al., *Biochem* 27:6268 (1988).
Thompson, C. B., *Science* 267:1456 (1995).
Verhoven, B., et al., *J. Experimental Med.* 182:1597 (1995).

Wang, Z. Q., et al., *European Journal of Immunology* 24:1549 (1994).

Williamson, P., and Schleel, R. A., *Molecular Membrane Biology* 11:199 (1994).

Wood, B. L., et al., *Blood* 88:1873–1880 (1996).

Woodley, S. L., et al., Transplantation 56:1443–1447 (1993).

Young, T. L. & Santella, R. M., *Carcinogenesis* 9:589–592 (1988).

Zwaal, R. F. A., and Schroit, A. J., Blood 89(4): 1121–1132 (1997).

Zwaal, R. F. A., et al., *Biochem. Soc. Trans.* 21:248 (1993).

BACKGROUND OF THE INVENTION

Apoptotic or programmed cell death plays a crucial role in development and a number of homeostatic and disease processes (Thompson, 1995). New therapeutic strategies of a variety of diseases may therefore be possible through the modulation of apoptotic cell death. The study of new pharmacologic agents to promote or inhibit apoptotic cell death has been impeded by the lack of a noninvasive method(s) to detect and monitor apoptotic cell death in vivo.

Lipid proton nuclear magnetic resonance spectroscopy ($^1$H NMRS) has been found to be useful in the detection of the specific changes of composition and/or fluidity of the plasma membrane of lymphoblasts and other cell lines undergoing apoptotic cell death (Blankenberg, et al., 1996). Clinical use of lipid $^1$H NMRS study apoptosis is currently limited by complex local magnetic microenvironments found naturally in many tissues and organs.

SUMMARY OF THE INVENTION

In one aspect, the present invention includes a method of imaging cell death (e.g., cell death due to apoptosis or necrosis) in a region of a mammalian subject in vivo. The method includes the steps of (a) administering to the subject, annexin coupled, e.g., directly or indirectly, to a biocompatible radionuclide, (b) after a period of time in which the labeled annexin can achieve localization in the subject, positioning the subject within the detection field of a radiation detector device, and (c) measuring radiation emission from the radionuclide localized in the subject, with the radiation detector device, to construct an image of radiation emission, where the image is a representation of cell death in the region of the mammalian subject. In one embodiment, the method further includes a step (d) of processing the image to subtract signal resulting from non-specific localization of the labeled annexin, such as non-specific localization in the kidney.

Radionuclides useful with the method include Iodine 123, Iodine 131, Gallium 67, Indium 111, Fluorine 18, and Technetium 99 m (Tc99m). It will be appreciated that Fluorine 18 is a positron emitter, and is thus useful in positron emission tomography (PET). Iodine 123, Iodine 131, Gallium 67, Indium 111, and Technetium 99 m are useful with standard gamma emission detection. Tc99m is a preferred radionuclide for use with the methods of the invention. In a preferred embodiment, the Tc99m is linked to the annexin via hydrazino nicotinamide (HYNIC). Tc99m-labelled annexin is typically administered at a dose of between about 5 and about 20 mCi.

In one general embodiment of the invention, the radiation detector device is a gamma ray detector device and the measured radiation emission is gamma ray emission. In another general embodiment, the radiation detector device is a positron emission detector device and the measured radiation emission is positron emission.

In yet another general embodiment, the method further includes repeating steps (b) and (c) at selected intervals, where the repeating is effective to track changes in the intensity of radiation emission (e.g., gamma ray or positron emission) from the region over time, reflecting changes in the number of cells undergoing cell death.

Still another general embodiment includes repeating steps (b) and (c) at selected intervals, where the repeating is effective to track changes in the localization of gamma ray emission in the region overtime, reflecting changes in the location of cells undergoing cell death.

The radiation detector device may be, for example, an Anger gamma scintillation camera or a 3-dimensional imaging camera.

A preferred annexin for use with the invention is annexin V. It is typically administered at doses less than about 300 µg protein/kg, preferably between about 1 and 10 µg protein/kg. Several administration routes are possible, including intravenous (i.v.), intraperitoneal (i.p.), intrathecal, and intrapleural administration.

The measuring of gamma ray emission to construct an image is typically done between about 5 minutes and about 2 hours after administration of the labelled annexin. In one embodiment, the measuring of gamma ray emission to construct the image is done about 1 hour after administration of the labelled annexin.

Different portions of the subject may be imaged using the method disclosed herein. For example, the region may include substantially the whole subject, or a portion of the subject, such as the head or portion thereof, the heart or portion thereof, the liver or portion thereof, and the like.

The invention also provides a kit for imaging cell death in vivo. The kit includes (i) a sealed vial containing HYNIC-labeled annexin, prepared, for example, as described in Materials and Methods (A), (ii) a sealed vial containing a Sn-tricine solution prepared, for example, as described in Materials and Methods (B), and maintained under $N_2$, (iii) instructions for making Tc-99m labeled annexin using the components of (I) and (ii) along with Tc-99m, and (iv) instructions for administering the Tc-99m annexin to image areas of cell death in vivo. In one embodiment, the kit is maintained at −70° C. and shipped on dry ice. In another embodiment, the HYNIC-labeled annexin is lyophilized.

In another aspect, the present invention provides a composition comprising an annexin, e.g., annexin V, coupled, e.g., directly or indirectly, with a therapeutic radioisotope, e.g., $^{103}$Pd, $^{186}$Re, $^{188}$Re, $^{90}$Y, $^{153}$Sm, $^{159}$Gd, or $^{166}$Ho. The therapeutic radioisotope and the annexin may be coupled at a ratio of 1:1, 1.1:1, 1.2:1, 1.3:1, 1.4:1, 1.5:1, 1.6:1, 1.7:1, 1.8:1, 1.9:1, or 2:1 (therapeutic radioisotope:annexin). Ranges of values using a combination of any of the above recited values as upper and/or lower limits are intended to be included in the present invention. In one embodiment, the annexin is coupled to a therapeutic radioisotope via a polymeric structure, e.g., dextran or variants thereof.

In a further aspect, the present invention provides a method of tumor radiotherapy by administering to a mammalian subject having a tumor an effective tumor reducing amount of a composition comprising an annexin coupled, e.g., directly or indirectly, with a therapeutic radioisotope. The foregoing method may be used in conjunction with total body irradiation or targeted external irradiation or internal irradiation (e.g., brachytherapy) and/or a treatment employing at least one chemotherapeutic agent (e.g., dimethyl busulfan, cyclophosphamide, bischloroethyl nitrosourea, cytosine arabinoside, or 6-thioguanine). In addition, the method may be used in conjunction with biologically active anti-cancer agents and apoptosis inducing agents such as TNF, TRAIL or Fas or with antibodies, small molecules or pharmacophores which bind these receptors and also induce apoptosis.

In another aspect, the present invention features a method of tumor radiotherapy, which includes treating a subject having a tumor with a chemotherapeutic agent and subsequently administering to the subject an effective tumor reducing amount of a composition comprising an annexin coupled with a therapeutic radioisotope.

The timing of the administration of the annexin coupled with a therapeutic agent is critical to the effectiveness of the therapeutic intervention. The modified annexin should be administered at a time which assures its bioavailability at times of apoptosis or necrosis of the target tissue. Diagnostic imaging studies using radiolabeled annexin V indicate that the administration of a therapeutically modified annexin preferably should be within 24 hours of the completion of a course of chemotherapy with multiple antimetabolite drugs (so-called, CHOP or MOPP therapy) to optimize the availability of annexin localization in the damaged tumor. Optimal time of administration may be within 36, 48, 60, or 72 hours of chemotherapeutic treatment of solid tumors such as breast cancer, lung cancer or sarcoma as shown by imaging studies in patients. Use of a diagnostic imaging agent, such as radiolabeled annexin, to determine the extent of apoptosis may be used to qualify patients for administration of therapeutically modified annexin and to determine the optimal dose of therapeutically modified annexin.

In another aspect, the present invention provides a composition which includes an annexin, e.g., annexin V or a fragment thereof, coupled (directly or indirectly) with a toxin, e.g., *E. coli*, Salmonella Sp., Listeria Sp., ciguatoxin and related marine polyethers, and aflatoxin.

These and other objects and features of the invention will become more fully apparent when the following detailed description is read in conjunction with the accompanying drawings.

DETAILED DESCRIPTION OF THE INVENTION

I. Definitions

Figure 1:
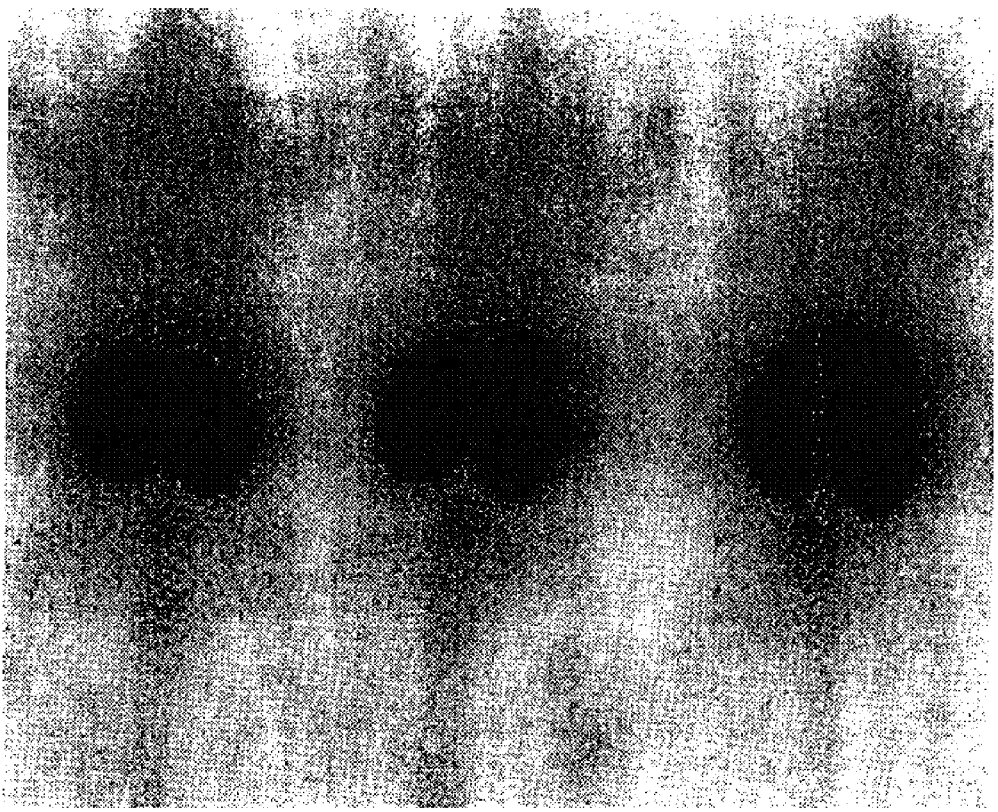
FIG. 1 is a computer-generated image showing Fas-mediated fulminant hepatic apoptosis as detected with Tc99m HYNIC-annexin V.

As used herein, the term "cell death" includes the processes by which mammalian cells die. Such processes include apoptosis (both reversible and irreversible) and processes thought to involve apoptosis (e.g., cell senescence), as well as necrosis. "Cell death" is used herein to refer to the death or imminent death of nucleated cells (e.g., neurons, myocytes, hepatocytes and the like) as well as to the death or imminent death of anucleate cells (e.g., red blood cells, platelets, and the like). Cell death is typically manifested by the exposure of PS on the outer leaflet of the plasma membrane.

As used herein, the term "subject" includes warm-blooded animals, preferably mammals, including humans. In a preferred embodiment, the subject is a primate. In an even more preferred embodiment, the subject is a human. Cell death may be imaged or detected in, for example, an organ of a subject or a portion thereof (e.g., brain, heart, liver lung, pancreas, colon) or a gland of a subject or a portion thereof (e.g., prostate, pituitary or mammary gland).

As used herein, the term "administering" to a subject includes dispensing, delivering or applying a composition of the invention to a subject by any suitable route for delivery of the composition to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route.

The compositions of the invention may be administered to a subject in an amount effective, at dosages and for periods of time necessary, to achieve the desired result. An effective amount of the compositions of the invention may vary according to factors such as disease state, e.g., the tumor stage, age, and weight of the subject, and the ability of the composition to elicit a desired response in the subject. An effective amount is also one in which any toxic or detrimental effects (e.g., side effects) of the compositions are outweighed by the therapeutically or diagnostically beneficial effects. The compositions of the invention may be administered at a concentration of, for example, 1–1000 $\mu$g protein/kg, 1–900 $\mu$g protein/kg, 1–800 $\mu$g protein/kg, 1–700 $\mu$g protein/kg, 1–600 $\mu$g protein/kg, 1–500 $\mu$g protein/kg, 1–400 $\mu$g protein/kg, 1–300 $\mu$g protein/kg, 1–200 $\mu$g protein/kg, 1–100 $\mu$g protein/kg, 10–100 $\mu$g protein/kg, 10–80 $\mu$g protein/kg, 10–60 $\mu$g protein/kg, 10–40 $\mu$g protein/kg, or 10–20 $\mu$g protein/kg.

A "biocompatible radionuclide" or "biocompatible radioisotope" is an isotope that is recognized as being useful for injection into a patient for nuclear medicine applications. Examples of biocompatible radionuclides include Iodine 123, Iodine 131, Gallium 67, Indium 111, Fluorine 18 and Technetium 99 m.

II. Cell Death—Apoptosis and Necrosis

Apoptosis refers to "programmed cell death" whereby the cell executes a "cell suicide" program. It is now thought that the apoptosis program is evolutionarily conserved among virtually all multicellular organisms, as well as among all the cells in a particular organism. Further, it is believed that in many cases, apoptosis may be a "default" program that must be actively inhibited in healthy surviving cells.

The decision by a cell to submit to apoptosis may be influenced by a variety of regulatory stimuli and environmental factors (Thompson, 1995). Physiological activators of apoptosis include tumor necrosis factor (TNF), Fas ligand, transforming growth factor $\beta$, the neurotransmitters glutamate, dopamine, N-methyl-D-asparate, withdrawal of growth factors, loss of matrix attachment, calcium and glucocorticoids. Damage-related inducers of apoptosis include heat shock, viral infection, bacterial toxins, the oncogenes myc, rel and E1A, tumor suppressor p53, cytolytic T-cells, oxidants, free radicals and nutrient deprivation (antimetabolites). Therapy-associated apoptosis inducers include gamma radiation, UV radiation and a variety of chemotherapeutic drugs, including cisplatin, doxorubicin, bleomycin, cytosine arabinoside, nitrogen mustard, methotrexate and vincristine. Toxin-related inducers or apoptosis include ethanol and d-amyloid peptide. Apoptosis can have particularly devastating consequences when it occurs pathologically in cells that do not normally regenerate, such as neurons. Because such cells are not replaced when they die, their loss can lead to debilitating and sometimes fatal dysfunction of the affected organ. Such dysfunction is evidenced in a number of neurodegenerative disorders that have been associated with increased apoptosis, including Alzheimer's disease, Parkinson's disease, amyotrophic lateral sclerosis, retinitis pigmentosa and cerebellar degeneration.

The consequences of undesired apoptosis can be similarly devastating in other pathologies as well, including ischemic injury, such as typically occurs in cases of myocardial infarction, reperfusion injury and stroke. In particular, apoptosis is believed to play a central role in very delayed infarction after mild focal ischemia (Du, et al., 1996). Additional diseases associated with increased apoptosis include, but are not limited to, the following: AIDS; myelodysplatic syndromes, such as aplastic anemia; and toxin induced liver disease, including damage due to excessive alcohol consumption.

Necrosis is the localized death of cells or tissue due to causes other than apoptosis (i.e., other than the execution of the cell's intrinsic suicide program). Necrosis can be caused by traumatic injury, bacterial infection, acute hypoxia and the like. There is some overlap between the two types of cell death, in that some stimuli can cause either necrosis or apoptosis or some of both, depending on the severity of the injury.

III. Asymmetry of Biological Membranes

It is generally believed that biological membranes are asymmetric with respect to specific membrane phospholipids. In particular, the outer leaflet of eukaryotic plasma membranes is formed predominantly with the cholinephospholipids, such as sphingomyelin and phosphatidylcholine (PC), whereas the inner leaflet contains predominantly aminophospholipids, such as phosphatidylserine (PS) and phosphatidylethanolamine (PE). This asymmetry is thought to be maintained by the activity of an adenosine triphosphate (ATP)-dependent aminophospholipid translocase, which selectively transports PS and PE between bilayer leaflets (Seigneuret and Devaux, 1984). Other enzymes thought to be involved in the transport of phospholipids between leaflets include ATP-dependent floppase (Connor, et al., 1992) and lipid scramblase (Zwaal, et al., 1993).

Although asymmetry appears to be the rule for normal cells, the loss of such asymmetry is associated with certain physiological, as well as pathogenic, processes. For example, it has been recognized that membrane asymmetry, detected as appearance of PS on the outer leaflet of the plasma membrane ("PS exposure"), is one of the earliest manifestations of apoptosis, preceding DNA fragmentation, plasma membrane blebbing, and loss of membrane integrity (Martin, et al., 1995; Fadok, e! al., 1992).

Similar re-orientation has been observed in sickle cell disease (Lane, et al., 1994) "B-thalassemia (Borenstain-Ben Yashar, et al., 1993), platelet activation, and in some mutant tumor cell lines with defective PS transport. A gradual appearance of PS on the outer leaflet has also been observed to occur in aging red blood cells (Tait and Gibson, 1994). When the PS exposure on such cells reaches a threshold level, the cells are removed from circulation by macrophages (Pak and Fidler, 1991). All of the above conditions proximately culminate in the death of the affected cells (i.e., cells with significant PS exposure).

It will be appreciated that PS exposure is a component in both apoptosis and necrosis. Its role in the initial stages of apoptosis is summarized above. Once the apoptotic cell has reached the terminal stages of apoptosis (i.e., loss of membrane integrity), it will be appreciated that the PS in both plasma membrane leaflets will be "exposed" to the extracellular milieu. A similar situation exists in cell death by necrosis, where the loss of membrane integrity is either the initiating factor or occurs early in the necrotic cell death process; accordingly, such necrotic cells also have "exposed" PS, since both plasma membrane leaflets are "exposed".

IV. Annexin

The annexin family of proteins is useful in the practice of the present invention. Annexin V is normally found in high levels in the cytoplasm of a number of cells including placenta, Lymphocytes, monocytes, biliary and renal (cortical) tubular epithelium. Although the physiological function of annexins has not been fully elucidated, several properties of annexins make them useful as diagnostic and/or therapeutic agents. In particular, it has been discovered that annexins possess a very high affinity for anionic phospholipid surfaces, such as a membrane leaflet having an exposed surface of phosphatidylserine (PS).

V. Overview of Experimental Results

Experiments performed in support of the present invention have demonstrated that administration of radiolabeled annexin can be used to image cell death in vivo. For instance, experiments in Example 1 describe the imaging and quantification of Fas-mediated hepatocyte death in response to injection of purified Jo2 antibody in mice (Ogasawara, et al., 1993). Results of these experiments (see, e.g., FIG. 1) showed a two- and four-fold increase in hepatic uptake of radiolabeled annexin V at one and two hours, respectively, specifically due to Fas-mediated hepatocyte death following Jo2 antibody injection. A transient two-fold increase in splenic uptake early after treatment, which subsequently fell to control values, was also observed. This decline in signal from spleen may have been due to a rapid clearance of circulating and splenic lymphocytes in response to a burst of Fas-mediated apoptosis following treatment.

Annexin binding was also observed in the kidneys. However, this binding was present in the absence of any apoptosis-inducing stimulus, and in fact, decreased as the hepatocyte signal increased. The progressive reduction in the renal activity with time following anti-Fas Ab administration, together with increasing hepatic uptake in the same period, implies that the non-apoptotic-related renal affinity for annexin V is lower than that of apoptotic tissue. Renal cortical binding of injected annexin V may be in part due to annexin's cross reactivity with renal tubular phospholipid.

It will be noted that there was little renal excretion of labelled annexin, suggesting that the radiolabel (in this case, Tc99m), remained linked to the annexin for the duration of the experiments. Further, injected Tc99m-labeled annexin was rapidly cleared from the bloodstream, having a serum half-life of about 3–7 minutes. These factors allowed for imaging of the radiopharmaceutical signal 1 to 2 hours after its administration.

The above-described characteristics enable serial daily (or bi-daily) imaging studies each of which represent snapshot of apoptotic activity with a tissue or organ of interest at the time of injection of the radiolabeled annexin V.

VI. Imaging Cell Death In Vivo

The present invention includes, in one aspect, a method of imaging cell death (due, e.g., to apoptosis or necrosis) in a region of a mammalian subject in vivo. In the method, a radiolabeled annexin (e.g., technetium 99m-labeled annexin V) is administered to the subject. After a period of time in which the conjugate can achieve localization in the subject, the subject is placed within the detection field of a gamma ray detector device. The subject is maintained in a substantially immobilized condition while gamma ray emission from the technetium 99m is measured using the gamma ray detector device. Following the measuring phase, an image of gamma ray emission is constructed The image so constructed is then used to provide the attending clinician with a map or a localization of areas of cell death in the mammalian subject, or in the region of the mammalian subject that is being analyzed.

To facilitate interpretation of an image obtained using the above method, the image may be digitally processed to filter out background, noise and/or non-specific localization (e.g., kidney localization) of the annexin/Tc99m conjugate, as described in more detail below.

An advantage of the above method is that, by measuring the gamma ray emission and forming an image at selected intervals, the method can be used to track changes in the intensity of gamma ray emission from the subject over time, reflecting changes in the number of cells undergoing cell death. Such an approach may also be used to track changes in the localization of gamma ray emission from the subject over time, reflecting changes in the distribution of cells undergoing cell death.

A. Synthesis of Radiolabeled Annexin

The invention can be practiced using purified native, recombinant, or synthetically-prepared annexin. Annexin V, for example, may be conveniently purified from human placenta (Funakoshi, et al., 1987). Recombinant annexin offers several advantages, however, including ease of preparation and economic efficiency. A number of different annexins have been cloned from humans and other organisms. Their sequences are available in sequence databases, including GenBank.

The invention is preferably practiced using annexin V, for several reasons. First, annexin V is one of the most abundant annexins, (ii) it is simple to produce from natural or recombinant sources, and (iii) it has a high affinity for phospholipid membranes (Tait, et al., 1988). Human annexin V has a molecular weight of 36 kd and high affinity (kd=7 nmol/L) for phosphatidylserine (PS). The sequence of human annexin V can be obtained from GenBank under accession numbers U05760–U05770.

An exemplary expression system suitable for making annexin for use with the present invention is referred to in the Materials and Methods. It employs the pET12a expression vector (Novagen, Madison, Wis.) in *E. coli*.

Other bacterial expression vectors can be utilized as well. They include, e.g., the plasmid pGEX (Smith, et al., 1988) and its derivatives (e.g., the pGEX series from Pharmacia Biotech, Piscataway, N.J.). These vectors express the polypeptide sequences of a cloned insert fused in-frame with glutathione-S-transferase. Recombinant pGEX plasmids can be transformed into appropriate strains of *E. coli* and fusion protein production can be induced by the addition of IPTG (isopropyl-thio galactopyranoside). Solubilized recombinant fusion protein can them be purified from cell lysates of the induced cultures using glutathione agarose affinity chromatography according to standard methods (Ausubel, et al.). Other commercially-available expression systems include yeast expression systems, such as the Pichia expression kit from Invitrogen (San Diego, Calif.); baculovirus expression systems (Reilly, et al.; Beames, et al.; Clontech, Palo Alto Calif.); and mammalian cell expression systems (Clontech, Palo Alto Calif.; Gibco-BRL, Gaithersburg Md.).

A number of features can be engineered into the expression vectors, such as leader sequences which promote the secretion of the expressed sequences into culture medium. The recombinantly produced polypeptides are typically isolated from lysed cells or culture media.

Isolated recombinant polypeptides produced as described above may be purified by standard protein purification procedures, including differential precipitation, molecular sieve chromatography, ionexchange chromatography, isoelectric focusing, gel electrophoresis and affinity chromatography. Protein preparations can also be concentrated by, for example, filtration (Amicon, Danvers, Mass.).

Annexin produced as described above is then labeled with a selected radionuclide. The particular isotope selected will depend on the particular application of the claimed method.

The invention may be practiced with any one of a variety of radionuclides presently available. In selecting a suitable radionuclide, the practitioner will typically consider the particular application of the invention, along with factors common to nuclear imaging in general. Such factors include (i) minimum of particle emission, (ii) primary photon energy of between about 50 and 500 kEv, (iii) physical half-life greater that the time required to prepare material for administration, (iv) effective half life longer than the examination time, suitable chemical form and reactivity, low toxicity, and stability or near stability of annexin labeled with that radionuclide.

An exemplary radionuclide is Tc99m, which has a half-life of about 6 hours and can be used to label annexin to high specific activities. It fulfills most of the above criteria and is used in over 80% of nuclear medicine imaging procedures. Other isotopes which may be used include Iodine 123 (half-life of ~13.2 hours), Iodine 131 (half-life of ~8 days), Gallium 67 (half-life of ~78 hours), and Indium 111 (half-life of ~2.8 days).

Linking of the isotope to annexin can be accomplished using known techniques. For example, Tc99m can be linked to annexin through the use of a hydrazino nicotinamide (HYNIC) group, available, e.g., from AnorMED, Langley, British Columbia, Canada, as described below in the Materials and Methods section. Gallium 67 and Indium 111 can be used to radiolabel proteins using, for example, the method described by Hnatowich, et al., 1983, incorporated herein by reference.

Other methods for labeling proteins with radionuclides are known. For example, U.S. Pat. No. 5,552,525, issued Sep. 3, 1996 (Dean), teaches the making of technetium-99m (Tc-99m) labeled peptides. Methods for labeling peptides and polypeptides with Tc-99m are also disclosed in U.S. Pat. Nos. 5,443,815, and 5,508,020. Lind et al., (1990) teach Tc-99m labeled monoclonal antibodies. LaMuraglia, et al., (1989) teach $^{111}$In-labeled non-specific human immunoglobulin, and Fischman, et al., (1991) teach chemotactic formyl peptide (fMLF)—[111]In-labeled DTPA conjugates.

B. Administration of Radiolabeled Annexin

Radiolabeled annexin may be administered using standard protocols for administration of radiolabeled compounds. The dosage depends on two primary considerations: (i) the amount and type of radionuclide injected, and (ii) the amount of annexin protein injected.

Technetium 99m can be administered to adult humans at doses up to about 20 mCi. The preferred dose for a single Tc99m administration is between about 5 and 20 mCi.

Annexin V begins to have pharmacological effects (anticoagulant effects) at doses greater than about 300 µg/kg. Accordingly, the diagnostic methods of the present invention (which seek to avoid pharmacological effects of the labeled annexin) are preferably practiced at doses lower than 300 µg/kg, typically less than about 50 µg/kg. Such tracer doses (e.g., 10 µg/kg to 50 µg/kg) have no reported pharmacologic or toxic side effects in animal or human subjects.

The radiolabeled annexin is typically suspended in a suitable delivery vehicle, such as sterile saline. The vehicle may also contain stabilizing agents, carriers, excipients, stabilizers, emulsifiers, and the like, as is recognized in the art.

Radiolabeled annexin can be administered by any of several routes known to be effective for administration of radiolabeled proteins for nuclear medicine imaging. A preferred method of administration is intravenous (i.v.) injection. It is particularly suitable for imaging of well-vascularized internal organs, such as the heart, liver, spleen, etc, Methods for i.v. injection of radiopharmaceuticals are known. For example, it is recognized that a radiolabeled pharmaceutical is typically administered as a bolus injection using either the Oldendorf/Tourniquet method or the intravenous push method (see, e.g., Mettler and Guierbteau, 1985).

For imaging the brain, the labeled annexin can be administered intrathecally. Intrathecal administration delivers compound directly to the sub-arachnoid space containing cerebral spinal fluid (CSF). Delivery to spinal cord regions can also be accomplished by epidural injection to a region of the spinal cord exterior to the arachnoid membrane.

For bronchoscopy applications, the annexin compounds of the present invention may be administered by inhalation. For example, the annexin compounds may be delivered in the form of an aerosol spray from a pressured container or dispenser which contains a suitable propellant, e.g., a gas such as carbon dioxide, or a nebulizer.

Other modes of administration include intraperitoneal (e.g., for patients on kidney dialysis), and intrapleural administration. For specific applications, the invention contemplates additional modes of delivery, including intramuscular injection, subcutaneous, intralymphatic, insufflation, and oral, intravaginal and/or rectal administration.

Methods for practicing the modes of administration listed above are known in the art.

C. Localization of Radiolabeled Annexin

After the labeled annexin is administered, it is allowed to localize to the target tissue or organ. Localization in this context refers to a condition when either an equilibrium or a pseudo-steady state relationship between bound, "localized", and unbound, "free" labeled annexin within a subject has been achieved. The amount of time required for such localization is typically on the order of minutes to tens of minutes. It can be estimated by the serum half-life of the labeled annexin. The localization time also depends on the accessibility of the target tissue to the labeled annexin. This in turn depends on the mode of administration, as is recognized in the art.

Imaging is preferably initiated after most of the labeled annexin has localized to its target(s). For i.v. administered Tc99m-labeled annexin V, this occurs after several half-lives. A duration of about 10 half-lives (about 30–240 min in the case of annexin/Tc99m conjugates) is considered to be ample time to achieve essentially complete localization. One of skill in the art will appreciate, however, that it may be desirable to perform the imaging at times less than or greater than the ~10 half-life timepoint described above. For example, in imaging cell death due to blood vessel injury, the accessibility of the target tissue is very high, such that a strong signal can be obtained from the target site in only a few minutes, especially if a low dose of labeled annexin is administered gradually to minimize signal from circulating label.

In all of the above cases, a reasonable estimate of the time to achieve localization may be made by one skilled in the art. Furthermore, the state of localization as a function of time may be followed by imaging the gamma ray signal from the labeled annexin according to the methods of the invention.

D. Gamma Ray Detection Devices

Gamma ray imaging devices function by accumulating signal arising from gamma rays emitted from the subject over time. One of the most widely-used methods for gamma ray detection is the Anger gamma scintillation camera (Mettler and Guiberteau, 1985). It operates by converting gamma rays emitted by the radionuclide into photons (usually with NaI(TI) crystals), which are then amplified in photomultiplier tubes (PMTs), converted to a voltage signal, and used to construct an image. The components of an Anger scintillation camera typically include a collimator, a scintillation crystal, an array of PMTs, a pulse height analyzer, a cathode ray tube (CRT), and a control console. The camera system also typically includes a computer. The processing between the PMs and the display (e.g., CRT) can be either analog or digital. A detailed description of the theory and operation of Anger gamma E. Placing Subject in the Field of a Gamma Ray Detection Device 1. Detection Field of Device. The detection of the device is defined as the area from which consistent and reliable measurements of gamma ray can be obtained. If ECT is being used to generate the image, the detection of the device is the entire space from which gamma ray emission can be reliably measured, or the portion of such space that the ECT system is programmed to include in the scan. This space is typically substantial larger than the detection field of a signal, non-ECT camera.

It will be understood that the entire animal or subject need not necessarily be in the detection field of gamma ray detection device. For example, if one is interested in analyzing the signal from a particular organ, only signal from the region containing the organ, and a sufficient surrounding "dark" zone, need be measured to obtain the desired information.

2. Placing the Subject: Immobilization. To collect the signal which is used to generate an image, the subject is located in the detection field of the photodetection devices during the period that gamma rays which will be used to construct an image are being measured. If the signal is sufficiently strong that an image can be constructed from gamma ray emission measured in less than about 20 milliseconds, and/or the subject does not move relative to the imaging plane sufficiently to substantially deteriorate the image, no special immobilization precautions are typically required. All that is required is that the subject be located in the field of the detection device for the extent of the measuring period.

If, on the other hand, the gamma ray emission measurement takes longer than about 20 msec, and the subject is agitated, precautions to insure immobilization of the subject during gamma ray emission measurement, commensurate with the degree of agitation of the subject, should be considered to preserve the spatial information in the constructed image. For example, in a case where the subject is a person and photon emission measurement time is on the order of a few seconds, the subject may simply be asked to remain as still as possible during gamma ray emission measurement (imaging). On the other hand, if the subject is an animal, such as a mouse, the subject can be immobilized using, for example, an anesthetic or a mechanical restraining device.

A variety of restraining devices may be constructed. For example, a restraining device effective to immobilize a mouse for tens of seconds to minutes may be built by fastening a sheet transparent to gamma rays over a foam cushion. The cushion has an indentation for the animal's head at one end. The animal is placed under the sheet such that its head is over the indentation, allowing it to breathe freely, yet the movement of its body is constrained by the foam cushion.

It will be understood that the region imaged may include substantially the entire subject, or only a part of the subject which needs to be diagnosed or monitored for cell death. For example, the region may include only an appendage or part of such appendage, the head, the central nervous system or an internal cavity, such as the thoracic or peritoneal cavity. In specific embodiments, the regions may contain only a selected organ or portion thereof. For example, the method may be applied to analysis of cell death only in the central nervous system, brain, heart, liver, spleen, lungs, bone marrow, or a portion of any of the above. Further, the region analyzed may be restricted to a tumor, e.g., in a cancer patient undergoing treatment designed to cause cell death in the tumor.

F. Constructing an Image of Gamma Ray Emission; Image Processing

In most suitable cameras, the measurement of gamma ray emission generates a voltage signal which can either be displayed on a CRT or stored and/or analyzed by a computer as an array of numbers. These numbers are used to generate an image by standard imaging methods. For example, the image is typically analyzed by normalizing the gamma ray counts (either to a fixed, pre-selected value, or to the maximum number detected in any pixel) and converting the normalized number to a brightness (greyscale) or to a color (pseudocolor) that is displayed on a monitor. In a pseudo-color representation, typical color assignments are as follows. Pixels with zero counts are assigned black, low counts blue, and increasing counts colors of increasing wavelength, on up to red for the highest gamma ray count values. The location of colors on the monitor represents the distribution of gamma ray emission, and, accordingly, the location of areas of cell death.

If it is desired to follow the localization and/or the signal over time, for example, to record the effects of a treatment on the distribution and/or localization of cell death, the measurement of gamma ray emission, or imaging can be repeated at selected time intervals to construct a series of images. The intervals can be as short as minutes, or as long as days, weeks, months or years.

Images generated by methods of the present invention may be analyzed by a variety of methods. They range from a simple visual examination, mental evaluation and/or printing of a hardcopy, to sophisticated digital image analysis.

VII. Applications

Major uses for radiolabeled annexin V include the detection of inappropriate apoptosis in disease states where it should not occur, e.g., immune disorders such as Lupus, transplant rejection, or in cells subject to severe ischemia; and the detection of insufficient apoptosis when it should occur, e.g., tumors or cells infected with virus.

The results described herein indicate that radiolabeled annexin can be employed in a variety of clinical settings in which apoptotic and/or necrotic cell death need to be monitored, such as, without limitation, organ and bone marrow transplant rejection or injury, infectious and non-infectious inflammatory diseases, autoimmune disease, cerebral and myocardial infarction and ischemia, cardiomyopathies, atherosclerative disease, neural and neuromuscular degenerative diseases, sickle cell disease, β-thalassemia, cancer therapy, AIDS, myelodysplastic syndromes, and toxin-induced liver disease, etc. Radiolabeled annexin may also be useful as a clinical research tool to study the normal immune system, embryological development, and immune tolerance and allergy.

Radiolabeled annexin V can be used, for example, to image and quantify apoptotic cell death in normal and malignant tissues undergoing treatment. Monitoring apoptosis with serial imaging studies using radiolabeled annexin V can be used for the rapid testing and development of new drugs and therapies in a variety of diseases. In addition, the methods may be used to monitor the progress of treatment, monitor the progress of disease, or both. Further, they may be used to aid in early detection of certain diseases.

The compositions and methods of the present invention may also be used in the diagnosis and/or treatment of subjects suffering from an eye disease, such as, for example, retinal disease or glaucoma.

In summary, the compositions and methods of the present invention provide a number of clinical and diagnostic benefits. For example, using the methods of the invention, the response of individual patients to established therapeutic anti-cancer regimens may be efficiently and timely evaluated; the anti-neoplastic activity of new anti-cancer drugs may be evaluated; the optimal dose and dosing schedules for new anti-cancer drugs may be identified; and the optimal dose and dosing schedules for existing anti-cancer drugs and drug combinations may be identified. In addition, using the methods of the invention, cancer patients in clinical trials may be categorized efficiently into responders and non-responders to therapeutic regimens.

The methods of the invention provide, among other things, a non-invasive technique for evaluating the early response of individual patient tumors to chemotherapy. This facilitates the selection of effective treatment by allowing rapid identification of ineffective treatments whose side effects might not be balanced by expected benefits.

The invention is further illustrated by the following examples, which should not be construed as further limiting. The contents of all references, pending patent applications and published patents, cited throughout this application, as well as the Figures are hereby expressly incorporated by reference.

Materials and Methods

A. Preparation of HYNIC Labeled Annexin V

Human annexin V was produced by expression in *E. coli* from the pET12a-PAPI plasmid and purified as previously described (Wood, et al., 1996, incorporated herein by reference). A 30 mM stock solution ("HYNIC ester stock") of the N-hydroxysuccinimide ester of hydrazino nicotinamide (HYNIC; obtained from AnorMED, Langley, British Columbia, Canada; Babich, et al., 1993, incorporated herein by reference) was prepared by suspending 220 µg of succinimidyl 6-hydrazinonicotinate hydrochloride (SHNH) in 18.5 pL of N, N-dimethyl formamide. Five mg of annexin V dissolved in 893 pL of Buffer A (20 mM HEPES, pH 7.4, 100 mM NaCl) were reacted with the HYNIC ester stock for three hours with gentle stirring shielded from light at room temperature according to the method described by Schwartz, et al., 1991, incorporated herein by reference. The reaction was quenched with 500 pL of 500 mM glycine pH 5.3 then dialyzed at 4° C. against 20 mM sodium citrate, pH 5.2, 100 mM NaCI. Precipitate was removed by centrifugation at 1500 xg for ten minutes. 100 μL (100 μg) aliquots of HYNIC-annexin V were stored at −70° C.

B. Radiolabeling of HYNIC-annexin V

80 μL of $SnCl_2$ (50 mg/ml in 0.1 N HCI purged for two hours with $N_2$ gas) was added to 50 ml of a 20 mM tricine solution (pH 7.1, purged for one hour with $N_2$ gas; tricine= N-[tris (hydroxymethyl) methyl glycine). 200 μL of the Sn-tricine solution was added to 100 μL of Tc99m (4–8 mCi activity) mixed with a 100 μL aliquot of annexin V (prepared as described above) according to the methods described by Larson, et al., 1995.

Specific activity of radiolabeled annexin was 20–200 μCi/μg protein (depending on desired activity) with radiopurity of 92%–97% determined with instant thin layer chromatography (ITLC) using saline as the solvent. Membrane binding activity of HYNIC-annexin V and decayed Tc99m HYNIC annexin V was determined by a modified competition assay in which 5 nM FITC-annexin V was substituted for $I^{125}$ annexin (Wood, et al., 1996). After 15 minutes at room temperature, the sample was centrifuged, the FITC-annexin V bound to the pelleted cells was released with EDTA and the released FITC-annexin V measured by fluorometry. In this assay system, unmodified annexin, HYNIC annexin, and Tc99m HYNIC annexin V had competitor inhibiting (50% concentrations of the binding of FITC-annexin V) of 8 nM, 10.5 nM, and 12.3 nM, respectively. Incorporation of HYNIC into annexin V was found to be 0.9 mol per mole of annexin V.

C. Imaging and Biodistribution Studies

Mice were injected with 50–150 μCi of Tc99m-HYNIC annexin (0.125–0.25 μg of protein) after determination of free versus bound Tc99m using ITLC saline as a solvent. Mice were imaged one to two hours after injection of radiopharmaceutical in the prone position. Images were acquired for 15 minutes using a Low Energy Mobile (LEM) scintillation camera with a high sensitivity parallel hole collimator and a 128×128 imaging matrix (Siemens, Des Plains, Ill.). The same protocols were used for all scans pre- and post-treatment.

Biodistribution studies were performed after harvesting specimens of cervical nodes/salivary glands, brain, thymus, heart, lungs, liver, spleen, stomach, GI tract, kidneys, skeletal muscle, fat, blood, and remaining carcass. Samples were counted on a Packard Cobra II autogamma scintillation counter (Packard Instrument, Downers Grove, Ill.) expressed as corrected counts per minute for isotope decay and background activity.

D. Immunostaining for Bound Human Annexin V and Apoptotic Nuclei

Formalin-fixed paraffin-embedded tissues were sectioned at 5 μm for staining with hematoxylin/eosin or other techniques. Immunostaining for bound human annexin V was performed with a rabbit anti-serum raised against human placental annexin V and affinity purified with recombinant annexin V coupled to Affi-Gel (Bio-Rad). Immunohistochemical detection then was completed by sequential incubations with biotin-labeled goat anti-rabbit antibody and avidin-horseradish peroxidase complex (Jackson Immuno Research), followed by reaction with 3,3'-diaminobenzidine as described by Bindl and Warnke (Bindl, J. M. & Warnke, R. A., 1986, incorporated herein by reference).

For the detection of apoptotic nuclei, sections were stained using a modification of the terminal deoxynucleotidyltransferase-mediated UTP end labeling (TUNEL) method described by Gavrieli et al. (Gavrieli, et al., 1992, incorporated herein by reference). After inhibition of endogenous peroxidase, deparaffinized sections were digested with proteinase K (20 μg/ml) for 15 min at room temperature. Sections were then incubated with λ exonuclease (Life Technologies Gaithersburg, Md.) at 5 unit/ml for 30 min at 37° C. followed by equilibration with terminal deoxynucleotidyltransferase reaction buffer (0.2 M potassium cacodylate, 25 mM TrisHCL, 0.25 mg/ml BSA, 1.5 mM $Cacl_2$, 20 mg/ml polyvinylpyrrolidone, and 20 mg/ml Ficoll) and 5 μM dATP. The end-labeling reaction then was performed in terminal deoxynucleotidyltransferase reaction buffer also containing a final concentration of 75 unit/ml of terminal deoxynucleotidyltransferase and 100 μM of 1,N-6-ethenol-dATP (Sigma). After a 60-min incubation at 37° C., the reaction was quenched via rinsing with 1× SSC (standard saline citrate). Sections were then incubated with murine 1G4 mAb (gift from Regina Santella, Columbia University), which recognizes the ethenoadenine moiety (Young, T. L. & Santella, R. M., 1988, incorporated herein by reference). Subsequent immuno-histochemical detection was as described above, using a biotin-labeled goat anti-mouse antibody.

EXAMPLE 1

In vivo Imaging of Fas-Mediated Apoptosis

Liver apoptosis in mice was induced by injection of anti-Fas antibody, which causes extensive liver apoptosis within one to two hours followed by death at three hours in 90% of treated animals (Ogasawara).

Five to six week old 18–24 gram female Balb/c mice were injected intravenously (i.v.) with purified hamster monoclonal anti-Fas antibody (Jo2, 10 μg per animal, Pharmingen, San Diego, Calif.). Following injection with the anti-Fas antibody, the animals were injected intravenously with about 90 μCi of technetium 99 m (Tc99m) hydrazino nicotinamide (HYNIC) radiolabeled annexin V at 0, 1, and 2 hours following antibody administration in three separate experiments. The results are shown in FIG. 1.

A marked progressive increase in hepatic uptake of radiolabeled annexin V was observed at one and two hours, corresponding to 148% and 372% of control values, respectively, as determined by the region-of-interest (ROI) image analysis illustrated in FIG. 1. Splenic uptake transiently rose to 140% of control values at one hour following treatment falling to 110% at two hours. Renal uptake fell 40% at one and two hours after treatment.

Figure 2:
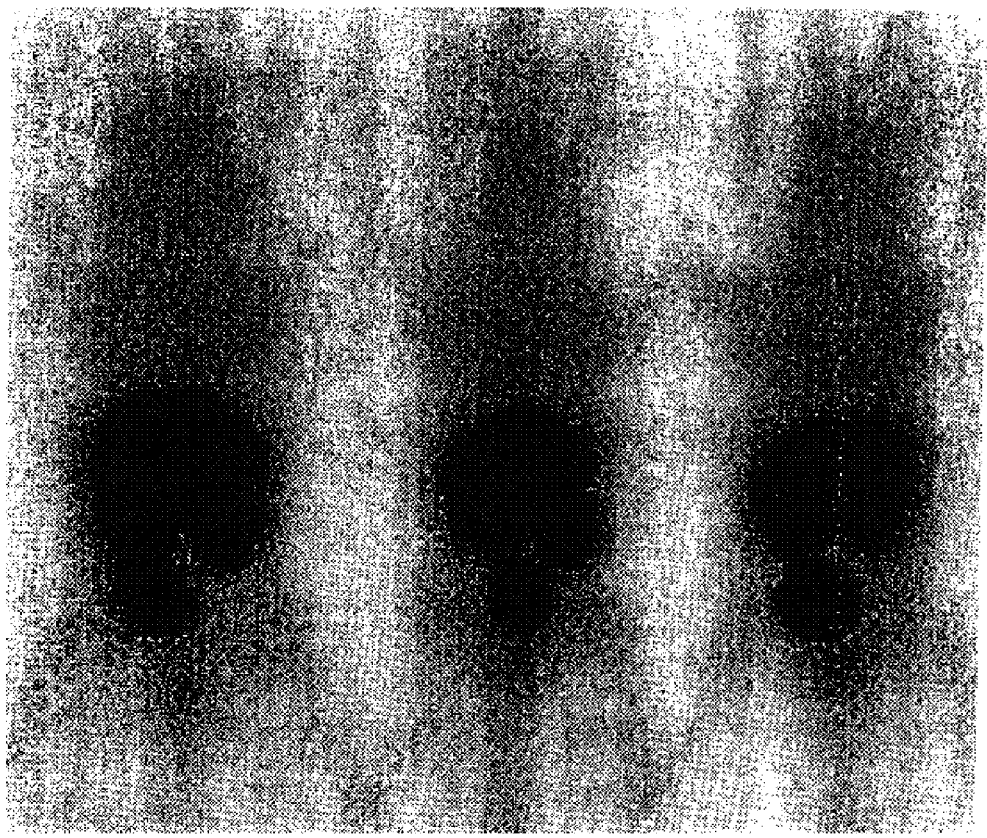
FIG. 2 is a computer-generated image showing signal from Tc99m HYNIC-ovalbumin during Fas-mediated fulminant hepatic apoptosis.

Another group of mice (control) were injected with 90 μCi of Tc99m HYNIC ovalbumin (MW=43kd; 2 μg of protein) at 0, 1, and 2 hours after Jo2 antibody treatment. As shown in FIG. 2, these animals demonstrated an initial increase in hepatic uptake a one hour (127%) which remained unchanged at two hours (131%) after anti-Fas antibody treatment. Splenic uptake of radiolabeled ovalbumin remained unchanged from control values after treatment. Renal uptake of radiolabeled ovalbumin increased 138% at one hour and plateaued at 131% of control values at two hours following treatment.

A third group of mice were treated as above and co-injected with Tc99m labeled annexin V and $I^{125}$ labeled human serum albumin (HAS) at 0, 1 and 2 hours in three separate experiments. The animals in the different experiments were sacrified after each corresponding timepoint and underwent biodistribution study. The results, expressed as percent injected dose per gram of tissue (% ID/gm), are shown in Table 1, below. The data were proportional to those obtained by ROI image analysis for both radiolabeled annexin V and HSA.

TABLE 1

Biodistribution Assay of Radiolabeled Annexin V and HSA

| Tc99m Annexin V % I.D./gm | Controls (N = 6) | Anti-Fas Treated Mice (10 μg/mouse) | |
|---|---|---|---|
| | | 1 hr. (N = 8) | 2 hr. (N = 6) |
| Liver | 11.7 ± 1.35 | 15.0 ± 3.5* | 41.6 ± 10.0** |
| Kidney | 187.9 ± 21.8 | 127.7 ± 42.6* | 64.9 ± 37.5** |
| Spleen | 12.1 ± 1.08 | 20.8 ± 7.8* | 17.5 ± 7.55 (N.S.) |

| $I^{125}$ HAS % I.D./gm | Controls (N = 4) | Anti-Fas Treated Mice (10 μg/mouse) | |
|---|---|---|---|
| | | 1 hr. (N = 6) | 2 hr. (N = 5) |
| Liver | 3.87 ± 0.76 | 6.92 ± 1.81* | 6.87 ± 1.2** |
| Kidney | 4.6 ± 0.89 | 6.0 ± 0.42* | 5.84 ± 0.88** |
| Spleen | 3.2 ± 0.67 | 3.75 ± 0.86 (N.S.) | 3.42 ± 0.56 (N.S.) |

| Organ Weight (grams) | Controls (N = 6) | Anti-Fas Treated Mice | |
|---|---|---|---|
| | | 1 hr. (N = 8) | 2 hr. (N = 6 |
| Liver | 1.02 ± 0.086 | 1.41 ± 0.37** | 1.32 ± 0.25* |
| Kidney | 0.33 ± 0.061 | 0.34 ± 0.082 (N.S.) | 0.34 ± 0.048 (N.S.) |
| Spleen | 0.11 ± 0.023 | 0.12 ± 0.02 (N.S.) | 0.11 ± 0.018 (N.S.) |
| TOTAL BODY | 19.5 ± 1.1 | 20.7 ± 2.2 (N.S.) | 19.3 ± 1.6 N.S. |

\* Significantly (p, 0.05) different from control values.
\*\* Highly significant (p , 0.001) different from control values.
N.S. Not significantly different from control values.
N.B. statistical comparisons of average values were performed with a two-tailed Student's T-test.

EXAMPLE 2

In vivo Imaging of Cardiac Allograft Rejection $^{99m}$Tc HYNIC-annexin V was prepared substantially as described above. Imaging and biodistribution studies were conducted as above, except where specified otherwise.

Adult male ACI rats (250–350 g) received heterotopic cardiac allografts from PVG donors (obtained from Harlan-Sprague-Dawley) anastomosed to the hosts' abdominal aorta and inferior vena cava according to a modification of the technique of Ono and Lindsey (Woodley, et. al., 1993, incorporated herein by reference). Syngeneic cardiac isografts from ACI donors also were transplanted to the abdomens of host ACI rats. PVG cardiac allografts in ACI recipients using the model above begin to undergo rejection between 4 and 5 days post-transplantation as assessed by decreased pulsation to palpitation. Five days after transplantation all of the animals received 700–900 μCi of $^{99m}$Tc HYNIC-annexin V (10–20 μg protein/kg) via tail vein and were imaged 1 hour later. Animals were then sacrificed, and native and transplanted hearts underwent scintillation counting and hisopathologic studies.

All of the PVG cardiac allografts (n=4) were visualized easily with $^{99m}$Tc HYNIC-annexin V 5 days after transplantation. ACI syngeneic cardiac isografts (n=3) had no visible activity after injection of 99 mTc HYNIC-annexin with uptakes of radiopharmaceutical identical to native cardiac activity as confirmed by scintillation well counting. The percentage of whole body activity of PVG allografts was 213% above ACI isograft activity (P<0.005; using a two-tailed student's t test) determined by ROI image analysis. Scintillation well-counting assay revealed a greater than 11-fold increase in $^{99m}$Tc HYNIC-annexin V uptake in PVG allografts as compared with native heart activity. Sections of PVG cardiac allografts 5 days after transplantation showed a marked mononuclear inflammatory cell infiltrate in ail animals; no infiltrate was observed in syngeneic or native hearts. The infiltrate surrounded areas of myocardial injury and was associated with thrombosis of myocardial vessels. In the center of these areas, there was frank necrosis, with no staining by hematoxylin, but at the periphery, there were nuclei with changes of apoptosis as confirmed by TUNEL staining. Immunostaining for 99 mTc HYNIC-annexin V was observed in a granular pattern in cardiac myocytes at the junction of inflamed and necrotic areas; the nuclei of these cells were stained still by hematoxylin, further suggesting that they were apoptotic rather than necrotic. Anti-annexin V staining was far more extensive in terms of the number of positive myocytes and intensity compared with TUNEL. Anti-annexin staining was heavy and clumped in frankly necrotic areas as expected but was specific; no staining was observed in syngeneic or native hearts or in staining of allografted hearts in which the primary antibody was omitted.

In a separate, but similar, set of experiments, ACI rats (n=6 in each group) received heterotopic cardiac allografts from PVG donors. Syngeneic cardiac isografts from ACI donors (n=3 in each group) were transplanted to host ACI rats. Neither group received treatment for transplant rejection.

Groups of recipient rats underwent nuclear scanning at day 1, 2, 3, 4, 5, 6, and day 7 posttransplantation. 1.0 mCi $^{99m}$Tc HYNIC-annexin V was injected 1 hour prior to nuclear scanning. The PVG cardiac allografts were visualized easily with $^{99m}$Tc HYNIC-annexin V 4 days after transplantation. ACI syngeneic cardiac isografts had no visible activity after injection of $^{99m}$Tc HYNIC-annexin.

Figure 3:
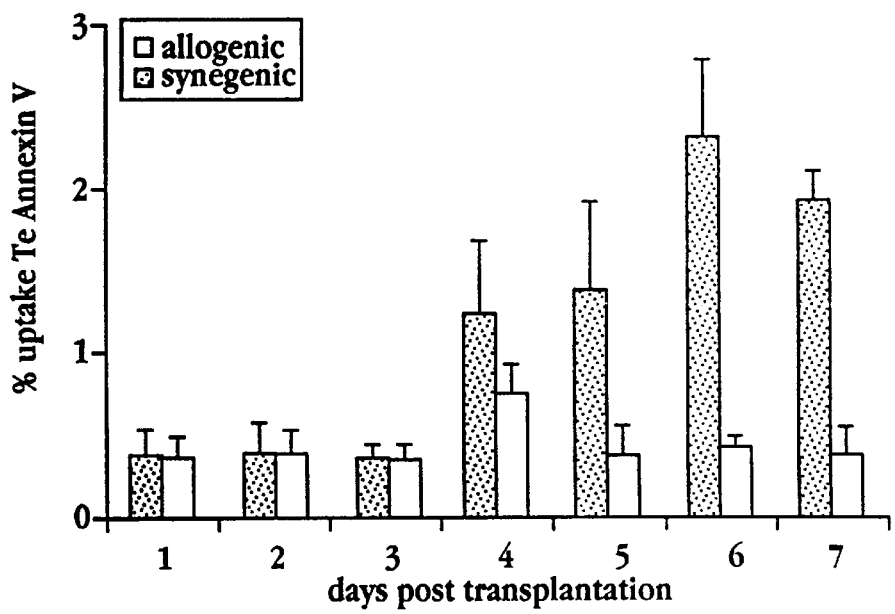
FIG. 3 is a graph depicting the uptake of Annexin V by an allogeneic or syngeneic transplanted heart.

Region of interest analysis was used to quantify uptake of $^{99m}$Tc HYNIC-annexin V. Uptake by the transplanted heart was calculated as percentage of total body uptake. The results are depicted in FIG. 3.

Immediately after nuclear scanning, animals were euthanized. Transplanted hearts were harvested for analysis. Histologic grading of acute rejection was performed on standard hematoxylin and eosin stained sections. The grading scheme is shown in Table 2, below.

TABLE 2

Histologic Grading of Acute Rejection

| Grade 0 | No Rejection |
| Grade 1 | Mild Rejection |
| Grade 2 | Moderate Rejection |
| Grade 3 | Severe Rejection |

Apoptotic nuclei were identified in histologic sections by TUNEL staining of nuclear DNA cleavage, using a commercially available peroxidase kit (APOPTAG®, Oncor, Gaithersburg, Md.). As indicated by the data of Table 3, apoptosis appears to occur in myocytes and inflammatory cells during cardiac allograft rejection.

TABLE 3

TUNEL Staining in Cardiac Allografts

Presence of Positive Nuclei during Rejection

Figure 4:
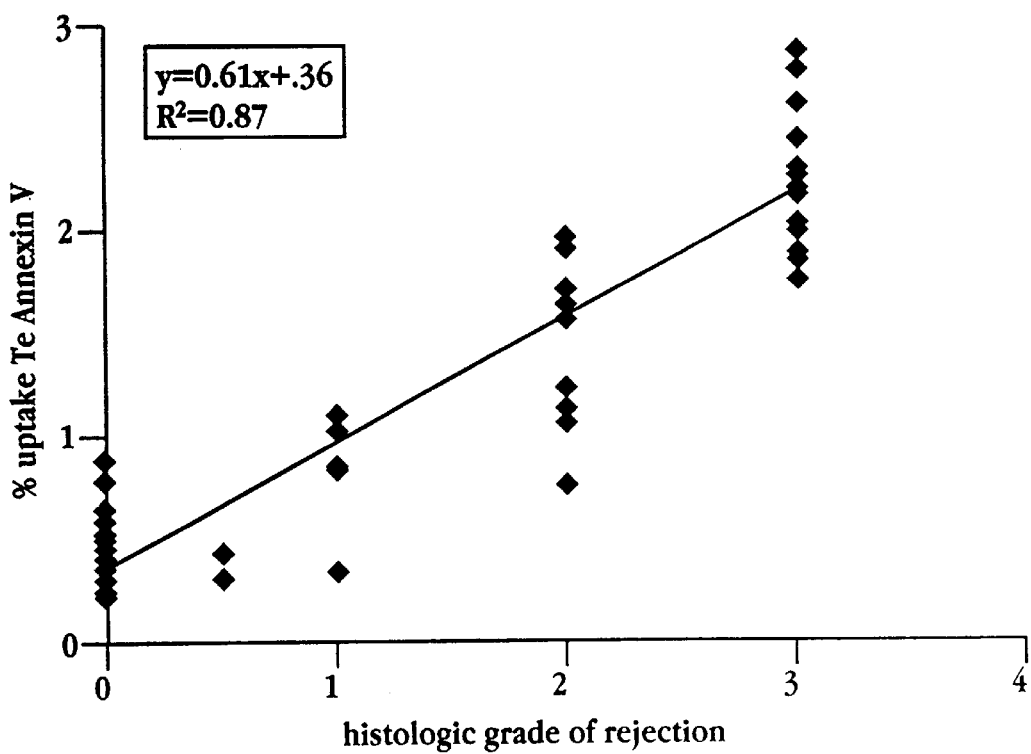
FIG. 4 is a graph depicting the uptake of Annexin V by a transplanted heart relative to a histologic grading of acute cardiac allograft rejection.

As shown by the data of Table 4, below, and the graph of FIG. 4, the uptake of $^{99m}$Tc HYNIC-annexin V correlates with histologic grades of acute rejection.

| Rejection | Inflammatory Cells | Endothelial Cells | Myocytes |
| --- | --- | --- | --- |
| Grade 0 | 0 | 0 | 0 |
| Grade 1 | + | + | + |
| Grade 2 | ++ | + | + |
| Grade 3 | + | + | ++ |

TABLE 4

Percent Uptake of 99mTc HYNIC-annexin V during Cardiac Allograft Rejection

| Rejection | % Uptake ± stdv | Significance * |
| --- | --- | --- |
| Grade 0 | 0.42 ± 0.17 | |
| Grade 1 | 0.83 ± 0.31 | P = 0.036 vs. Grade 0 |
| Grade 2 | 1.43 ± 0.40 | P = 0.008 vs. Grade 1 |
| Grade 3 | 2.40 ± 0.53 | P = 0.001 vs. Grade 2 |

* Student's t-test, two tailed, unequal variance

EXAMPLE 3

In vivo Imaging of Treated Murine Lymphoma $^{99m}$Tc HYNIC-annexin V was prepared substantially as described above. Imaging and biodistribution studies were conducted as above, except where specified otherwise.

38C13 murine B cell lymphomas (Maloney, et al., 1985) were grown in C3H.HeN mice (Harlan Breeders, Indianapolis) following s.c. injection of 400 tumor cells suspended in 200 μl of RPMI medium 1640 (without serum) into the left flank. Fourteen days after implantation mice underwent treatment with 100 mg/kg of cyclophosphamide injected i.p. Mice were injected i.v. with 25–50 μg/kg of $^{99m}$Tc HYNIC-annexin V (100–150 μCi/animal) 20 hours after cyclophosphamide administration. Animals were then imaged and sacrificed 1 hr after injection of radiophamaceutical after tumor removal for scintillation counting and histopathologic studies.

Untreated flank tumor implants (n=8) were seen easily by scintillation camera imaging and had an annexin V uptake 365% above normal soft tissue activity as shown by ROI image analysis. Treated flank tumors (n=6) showed readily visualizable increases in 99mTc HYNIC-annexin V activity of 78% above control values expressed as whole body activity per gram of tumor (P<0.05 using a two-tailed student's t test for significance). This result was confirmed by scintillation well counting in which treated tumors demonstrated a 132% increase in annexin V uptake expressed as percentage of injected dose per gram of tumor (P<0.05) with a 58% fall in weight (<0.05) compared with the control. The whole body activity per gram of tumor as seen by ROI image analysis linearly correlated to percentage of injected dose per gram of tumor determined on biodistribution study ($r^2$=0.831). Histologic analysis demonstrated virtually complete (greater than 95%) apoptosis of all lymphoblasts in treated tumors with less than 5% apoptotic cells in controls.

EXAMPLE 4

Binding of Radiolabeled Annexin V to Red Blood Cells

In these experiments, Hynic-Annexin was radiolabeled with either Tc-99m, resulting in a Tc-99m Hynic-Annexin preparation, or with Re-188, resulting in a Re-188 Hynic-Annexin preparation. Both preparations are tested for their ability to bind to red blood cells.

The radiolabeling that resulted in the two preparations was performed as follows:

Preparation #1: Hynic-Annexin research grade Lot #60-027 JLV032202, containing 100 μg Hynic-Annexin was reconstituted with 0.2 mL pertechnetate, 7.63 mCi. A stannous tricine vial was reconstituted with 0.5 mL of saline, and 0.1 mL was added to the preparation. After 15 min, 0.5 mL of saline was added.

Preparation #2: 0.5 mL of Re-188 perrhenate was added to a stannous tricine vial lyophilized kit. The Re-188 was allowed to incubate at room temperature for 5 minutes and, then 0.3 mL of this solution were transferred to a vial of Hynic-Annexin research grade Lot #60-027 JLV032202, containing 100 μg Hynic-Annexin.

Analysis of the radiolabeled products using chromatography, indicated successful labeling of Hynic-Annexin with both Tc-99m and Re-188.

For the red blood cell (RBC) assay, Annexin radiolabeled as indicated above, is incubated with red blood cells in the presence of calcium (as described in J. F. Tait et al. (2000) *Bioconjugate Chem.*, 11:918–25, the contents of which are incorporated herein by reference). Briefly, the radiolabeled protein preparation is added at a 10 nmol/L concentration to duplicate tubes containing a final volume of 250 μL. Subsequently, Coulter 4C Plus red cell normal control (12.5 to 50 μL, corresponding to $5 \times 10^7$ to $2 \times 10^8$ cells) is added to the tubes. A solution of CaCl2 (2.5 mM to 10 mM) and/or EDTA 50 mM is then added. Finally, an assay buffer made of 10 mM Hepes pH 7.4, 136 mM NaCl, 2.7 mM KCl, 2 mM MgCl2, 1 mM NaH2PO4, 5 mM glucose and 1 mg/mL bovine serum albumin is added to reach a total volume of 250 μL (typically 180 to 225 μL). After a 15 minute incubation at 37° C., the tubes are centrifuged for 5 minutes at 11,000 rpm. Radioactivity is measured in 50 μL of the supernatants.

The percentage of radioactivity bound to the cells is calculated using a two step analysis: First, the specific amount of binding is determined as follows:

[(supernatant counts in the presence of EDTA)–(supernatant in the absence of EDTA)]. Then, the % binding is determined as:

specific binding/(supernatant counts in the presence of EDTA)×100.

A % binding greater than about 70% indicates a bioactive radiolabeled annexin.

EXAMPLE 5

Conjugation of MAG3 to Annexin

Conjugation of MAG3 to Annexin is performed as described in, for example, Z. Zhu et al. (2001) *Nucl Med Biol.* 28:703–8 and Hnatowich D J et al. (1998) *J. Nucl. Med.* 39:56–64. Briefly, a fresh solution of NHS-MAG3 is prepared at a concentration of 10 to 50 mg/mL in dry DMF. This solution is then added dropwise to a solution of Annexin at 1 to 5 mg/mL in 0.1 M HEPES buffer pH 8, so that the final molar ratio of MAG3 to Annexin is about 5:1. The volume of DMF should always be less than 10% of the total volume. The reaction mixture is incubated at room temperature for 30 to 60 minutes and then purified on a Sephadex G25 column using 20 mM citrate buffer pH 5.5 as the eluant. The peak fractions are collected and quantitated by absorption at 280 μm, and stored at −20° C. until further use.

For the Tc-99m labeling of MAG3-Annexin, the following procedure is used. The MAG3-Annexin is typically used at a concentration of 300 to 500 μg/mL in citrate buffer. Aliquots of sodium tartrate in 0.5 M bicarbonate are added until a final concentration of 7 μg/μL and a pH of 9.2 are reached. Subsequently, 10 to 50 μCi of Tc-99m pertechnetate is added per μg of Annexin, and 4 μL of freshly prepared stannous chloride dihydrate (1 mg/mL in 0.01M HCl) is added per 10 μL of Tc99m. The solution is incubated at room temperature for 30–60 minutes. The final pH is approximately 7.5 and the labeled Annexin can be purified over a Sephadex G25 using 0.05 M PBS as an eluant.

For the Re-188 labeling of MAG3-Annexin, the following procedure is used. A 20 mg/mL citric acid solution is prepared, and Re-188 perrhenate is added in the proportion of 10 μL to 100 μL of citric acid solution. This solution is then added to the MAG3-Annexin, which is typically used at a concentration of 300 to 500 μg/mL in citrate buffer. After a 30–60 minute incubation at room temperature, the labeled Annexin can be purified over a Sephadex G25 using 0.05 M PBS/ascorbate as the eluant.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of tumor radiotherapy comprising administering to a mammalian subject having a tumor involving a nucleated cell an effective tumor reducing amount of a composition comprising an annexin coupled with a therapeutic radioisotope.

2. The method of claim 1, used in conjunction with total body irradiation or targeted external irradiation.

3. The method of claim 1, used in conjunction with targeted internal irradiation.

4. The method of claim 1, used in conjunction with a treatment employing at least one chemotherapeutic agent.

5. The method of claim 4, wherein the chemotherapeutic agent is selected from the group consisting of dimethyl busulfan, cyclophosphamide, bischloroethyl nitrosourea, cytosine arabinoside, and 6-thioguanine.

6. The method of claim 1, used in conjunction with total body irradiation and with a treatment employing at least one chemotherapeutic agent.

7. The method of claim 6, wherein the chemotherapeutic agent is selected from the group consisting of dimethyl busulfan, cyclophosphamide, bischloroethyl nitrosourea, cytosine arabinoside, and 6-thioguanine.

8. The method of claim 1, used in conjunction with an apoptosis inducing agent selected from the group consisting of TNF, TRAIL and Fas.

9. The method of claim 1, used in conjunction with an apoptosis inducing agent selected from the group consisting of a TNF-binding antibody, a TRAIL-binding antibody and a Fas-binding antibody.

10. The method of claim 1, wherein the therapeutic radioisotope is selected from the group consisting of $^{103}$Pd, $^{186}$Re, $^{188}$Re, $^{90}$Y, $^{153}$Sm, $^{159}$Gd, and $^{166}$Ho.

11. The method of claim 1, wherein the annexin is annexin V or a fragment thereof.

12. A method of tumor radiotherapy, comprising
treating a subject having a tumor involving a nucleated cell with a chemotherapeutic agent; and
administering to the treated subject an effective tumor reducing amount of a composition comprising an annexin coupled with a therapeutic radioisotope.

13. The method of claim 12, wherein the chemotherapeutic agent is selected from the group consisting of dimethyl busulfan, cyclophosphamide, bischloroethyl nitrosourea, cytosine arabinoside, and 6-thioguanine.

14. The method of claim 12, further comprising administering to the subject an apoptosis inducing agent selected from the group consisting of TNF, TRAIL and Fas.

15. The method of claim 12, further comprising administering to the subject an apoptosis inducing agent selected from the group consisting of a TNF-binding antibody, a TRAIL-binding antibody and a Fas-binding antibody.

16. The method of claim 12, wherein the therapeutic radioisotope is selected from the group consisting of $^{103}$Pd, $^{186}$Re, $^{188}$Re, $^{90}$Y, $^{153}$Sm, $^{159}$Gd, and $^{166}$Ho.

17. The method of claim 12, wherein the annexin is annexin V or a fragment thereof.

* * * * *